US00PP25570P2

(12) United States Plant Patent
van der Pligt

(10) Patent No.: US PP25,570 P2
(45) Date of Patent: May 19, 2015

(54) *BEGONIA* PLANT NAMED 'LYDIA'

(50) Latin Name: *Begonia hiemalis*
Varietal Denomination: LYDIA

(71) Applicant: Gert van der Pligt, Heinenoord (NL)

(72) Inventor: Gert van der Pligt, Heinenoord (NL)

(73) Assignee: Beeken Kamp Plants B.V., Maasdijk (NL)

( * ) Notice: Subject to any disclaimer, the term of this patent is extended or adjusted under 35 U.S.C. 154(b) by 80 days.

(21) Appl. No.: 13/815,612

(22) Filed: Mar. 11, 2013

(51) Int. Cl.
*A01H 5/00* (2006.01)

(52) U.S. Cl.
USPC ..... Plt./344

(58) Field of Classification Search
USPC ..... Plt./344
See application file for complete search history.

(56) References Cited

PUBLICATIONS

PLUTO Plant Variety Database 2014-04 search for *begonia* 'Lydia'.*

* cited by examiner

*Primary Examiner* — Annette Para
(74) *Attorney, Agent, or Firm* — C. A. Whealy

(57) ABSTRACT

A new and distinct cultivar of *Begonia* plant named 'LYDIA', characterized by its upright, somewhat outwardly spreading and mounded plant habit; basal branching habit; dark green-colored leaves; uniform and freely flowering habit; and double flowers that are yellow and orange in color.

2 Drawing Sheets

Botanical designation: *Begonia hiemalis*.
Cultivar denomination: 'LYDIA'.

BACKGROUND OF THE INVENTION

The present invention relates to a new and distinct cultivar of *Begonia* plant, botanically known as *Begonia hiemalis*, commercially referred to as a Elatior *Begonia* and hereinafter referred to by the name 'LYDIA'.

The new *Begonia* plant is a naturally-occurring whole plant mutation of *Begonia hiemalis* 'Nadine', disclosed in U.S. Plant patent application Ser. No. 10/008,292 (abandoned). The new *Begonia* plant was discovered and selected by the Inventor as a single flowering plant within a population of plants of 'Nadine' in a controlled greenhouse environment in Heinenoord, The Netherlands in March, 2010.

Asexual reproduction of the new *Begonia* plant by tip cuttings in a controlled greenhouse environment in Amstelveen, The Netherlands since February, 2011 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'LYDIA'. These characteristics in combination distinguish 'LYDIA' as a new and distinct *Begonia* plant:

1. Upright, somewhat outwardly spreading and mounded plant habit.
2. Basal branching habit.

3. Dark green-colored leaves.
4. Uniform and freely flowering habit.
5. Double flowers that are yellow and orange in color.

Plants of the new *Begonia* can be compared to plants of the mutation parent, 'Nadine'. Plants of the new *Begonia* differ primarily from plants of 'Nadine' in the following characteristics:

1. Plants of the new *Begonia* are more compact and denser than plants of 'Nadine'.
2. Flowers of plants of the new *Begonia* are double whereas flowers of plants of 'Nadine' are single.

Plants of the new *Begonia* can be compared to plants of the *Begonia* 'BBEVA', disclosed in U.S. Plant Pat. No. 16,053. In side-by-side comparisons conducted in 's-Gravenzande, The Netherlands, plants of the new *Begonia* differed from plants of 'BBEVA' in the following characteristics:

1. Plants of the new *Begonia* were larger than and not as compact as plants of 'BBEVA'.
2. Flowers of plants of the new *Begonia* had fewer tepals than flowers of plants of 'BBEVA'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'LYDIA' grown in a container.

The photograph on the second sheet are close up views of typical flower buds, flowers and leaves of 'LYDIA'.

DETAILED BOTANICAL DESCRIPTIONS

Plants used for the aforementioned photographs and following observations and measurements were grown in 13-cm containers during the summer in a glass-covered greenhouse in 's-Gravenzande, The Netherlands. During the production of the plants, day temperatures ranged from 20° to 21° C., night temperatures ranged from 19° to 20° C. and light levels averaged 7,000 lux. Plants were eleven weeks old when the photographs and the description were taken. In the following description, color references are made to The Royal Horticultural Society Colour Chart, 2007 Edition, except where general terms of ordinary dictionary significance are used.

Botanical classification: *Begonia hiemalis* 'LYDIA'.

Parentage: Naturally-occurring whole plant mutation of *Begonia hiemalis* 'Nadine', disclosed in U.S. Plant Patent application publication number 2003/6093846.

Propagation:

*Type*.—By tip cuttings.

*Time to initiate roots*.—About 20 days at temperatures about 25° C.

*Time to produce a rooted young plant*.—About 35 to 36 days at temperatures about 21° C. to 23° C.

*Root description*.—Medium in thickness, fibrous; light brown in color; plants of the new *Begonia* have not been observed to form tubers.

*Rooting habit*.—Moderate branching; medium density.

Plant description:

*Plant and growth habit*.—Upright, somewhat outwardly spreading and mounded plant habit; plant shape roughly broadly ovate; basal branching habit with about three basal branches per plant; moderately vigorous growth habit.

*Plant height*.—About 20.7 cm.

*Plant width*.—About 25 cm.

*Lateral branch description*.—Length: About 11.4 cm. Diameter: About 9 mm to 10 mm. Internode length: About 2.3 cm. Texture: Young stems, sparsely pubescent; developed stems, glabrous. Aspect: Upright to about 20° from the vertical. Color, developing: Close to between 144A and 146C. Color, fully developed: Close to between 144A and 146B.

*Leaf description*.—Arrangement: Alternate, simple. Length: About 13.6 cm. Width: About 9.4 cm. Shape: Broadly ovate, unequal. Apex: Broadly acute. Base: Oblique to hastate. Margin: Bi-serrate to denticulate. Texture, upper surface: Smooth, glabrous; velvety. Texture, lower surface: Sparsely pubescent along veins. Venation pattern: Palmate. Color: Developing leaves, upper surface: Between N137D and 141A. Developing leaves, lower surface: Close to 147B slightly tinged with close to 182B. Fully expanded leaves, upper surface: Between N137A and 147A; venation, close to 143B. Fully expanded leaves, lower surface: Close to 191A; venation, close to 144A. Petioles: Length: About 5.9 cm. Diameter: About 4.5 mm. Texture, upper and lower surfaces: Pubescent. Color, upper and lower surfaces: Close to 144C.

Flower description:

*Flowering habit*.—Fully double rotate flowers arranged in axillary compound cymes; flowers sterile; freely flowering habit with about ten flowers per cyme and about 300 flowers developing per plant; flowers face upright to outwardly.

*Fragrance*.—None detected.

*Natural flowering season*.—Plants begin flowering about ten weeks after planting; long flowering period, plants flower freely and continuously from spring into the autumn in The Netherlands.

*Flower longevity*.—Individual flowers last about ten days on the plant; flowers not persistent.

*Inflorescence height*.—About 11.1 cm.

*Inflorescence diameter*.—About 8.5 cm.

*Flower diameter*.—About 4.9 cm.

*Flower height*.—About 2.2 cm.

*Flower buds*.—Length: About 1.7 cm. Diameter: About 6 mm to 22 mm. Shape: Orbicular, flattened. Color: Close to 149D and 150D; upper margin, close to 154C to 154D.

*Tepals*.—Quantity per flower and arrangement: Two, opposite. Length: About 3 cm. Width: About 3.6 cm. Shape: Reniform. Apex: Rounded. Margin: Entire. Texture, upper surface: Smooth, glabrous; slightly velvety. Texture, lower surface: Smooth, glabrous. Color: When opening, upper surface: Close to 14C; towards the apex and margins, tinged with close to 22A to 22B; towards the base, close to 145C. When opening, lower surface: Close to 11B; center and towards the base, close to 145D. Fully opened, upper surface: Close to 24B; towards the apex and margins, close to 15D; towards the base, close to 154C; with development, color becoming closer to 15D and towards the apex, close to 33C. Fully opened, lower surface: Close to 19B; towards the base, close to 1D; with development, color towards the apex, becoming closer to 37A.

*Tepaloids*.—Quantity per flower and arrangement: About 25 in multiple whorls. Length: About 1.9 cm. Width: About 1.8 cm. Shape: Obovate. Apex: Rounded. Margin: Entire. Texture, upper surface: Smooth, glabrous; slightly velvety. Texture, lower surface: Smooth, glabrous. Color: When opening, upper surface: Close to 6B; towards the base, close to 4C. When opening, lower surface: Close to 10B to 10D. Fully opened, upper surface: Close to 25C; color does not fade with development. Fully opened, lower surface: Close to between 20C to 21D; color does not fade with development.

*Peduncles*.—Length: About 7.9 cm. Diameter: About 4 mm to 5 mm. Angle: About 30° from branch axis. Strength: Flexible, bending with the weight of the flowers. Texture: Smooth, glabrous. Color: Close to 144A.

*Pedicels*.—Length: About 2.5 cm. Diameter: About 2 mm. Angle: About 40° from the peduncle axis. Strength: Flexible, bending with the weight of the flowers. Texture: Smooth, glabrous. Color: Close to 11B; proximally, close to 144C.

*Reproductive organs*.—Androecium: Not observed on plants of the new *Begonia*. Gynoecium: Not observed on plants of the new *Begonia*.

Disease & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'LYDIA' as illustrated and described.

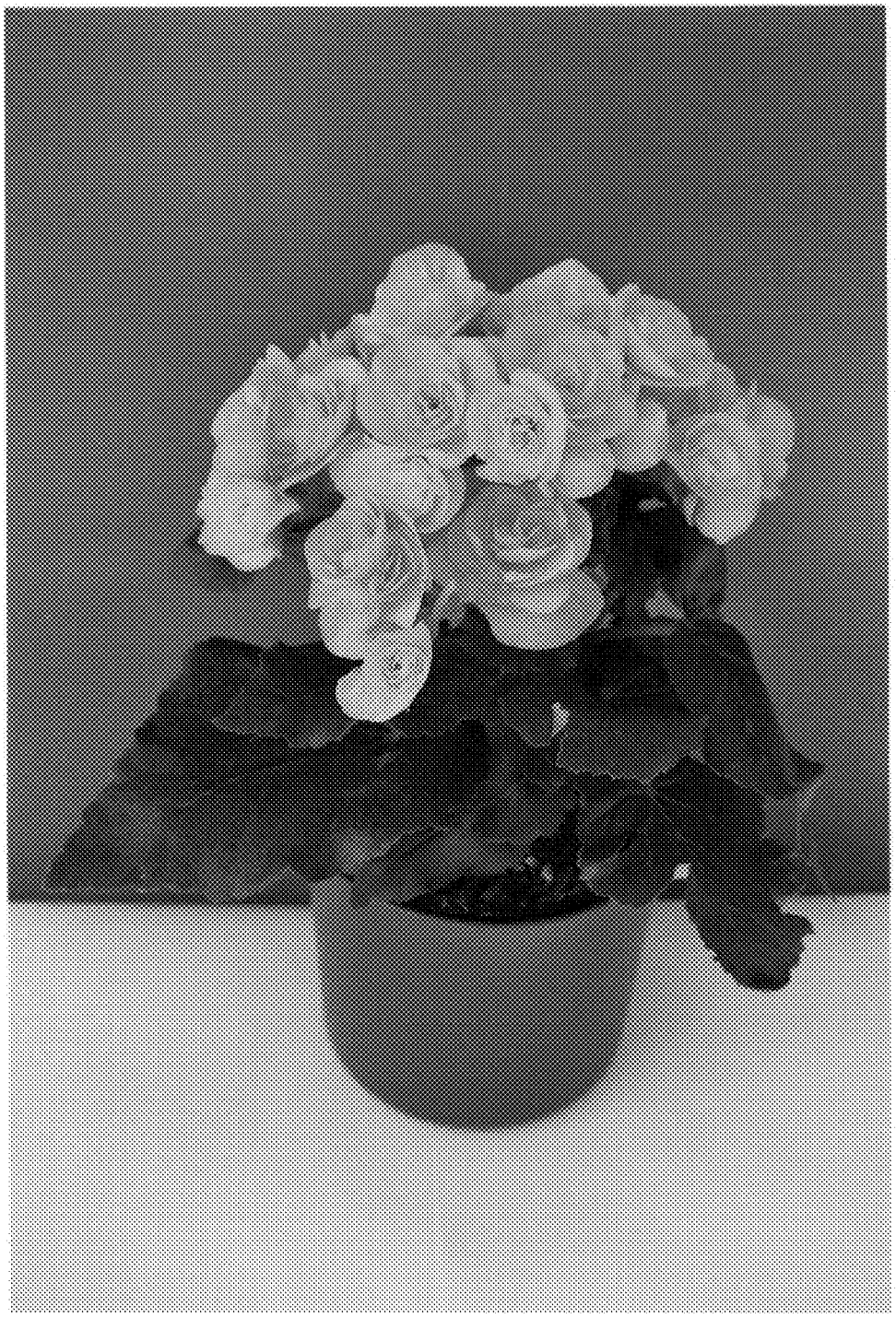

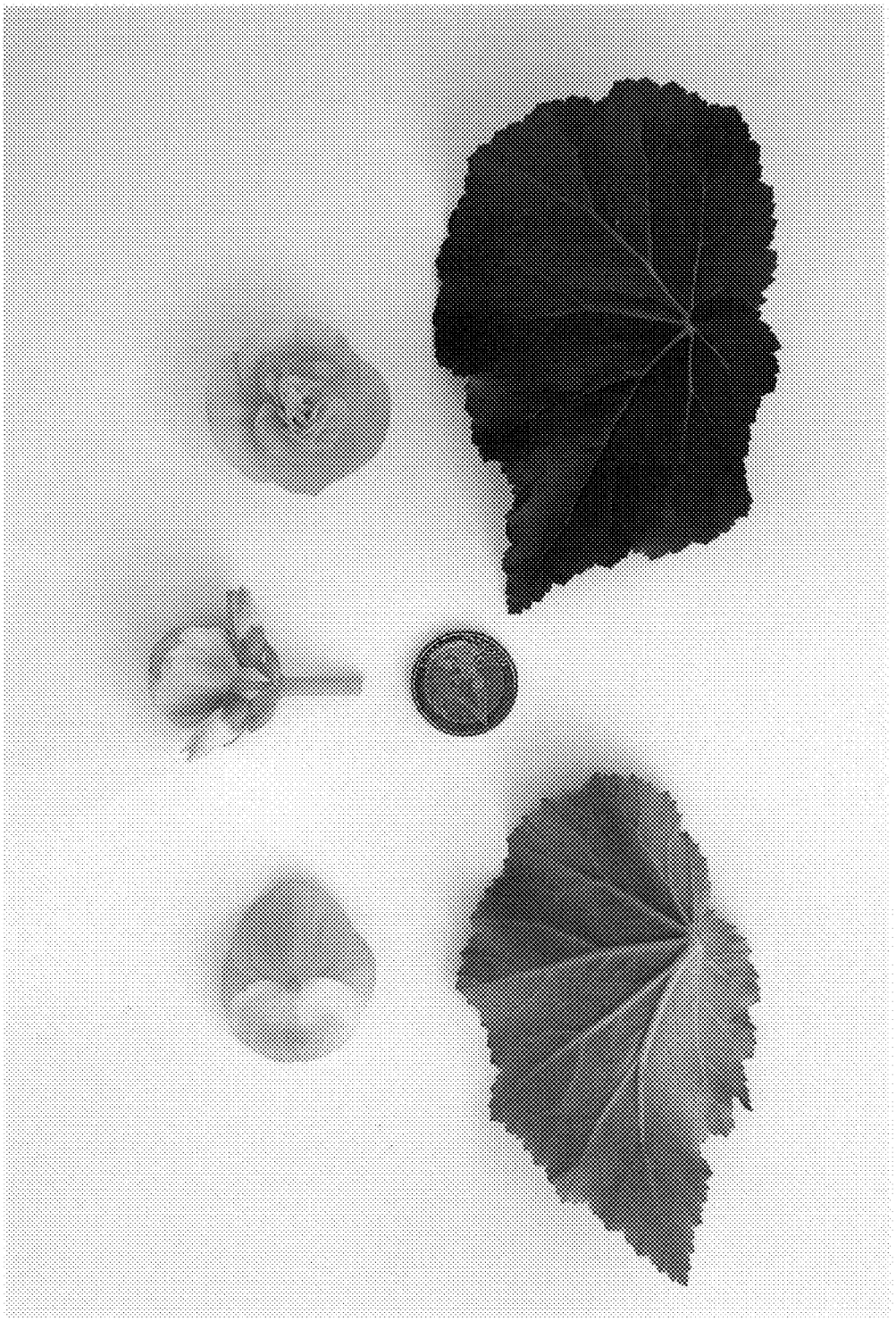

* * * * *